United States Patent [19]
Lalin

[11] Patent Number: 5,562,002
[45] Date of Patent: Oct. 8, 1996

[54] POSITIVE DISPLACEMENT PISTON FLOW METER WITH DAMPING ASSEMBLY

[75] Inventor: Hill S. Lalin, Wayne, N.J.

[73] Assignee: Sensidyne Inc., Clearwater, Fla.

[21] Appl. No.: 383,451

[22] Filed: Feb. 3, 1995

[51] Int. Cl.$^6$ .................................................. G01F 3/00
[52] U.S. Cl. ................................................ 73/241; 73/861
[58] Field of Search ................ 73/220, 861, 861.47, 73/241, 861.53, 861.54, 861.59, 861.72, 861.82

[56] References Cited

U.S. PATENT DOCUMENTS

| | | | |
|---|---|---|---|
| 4,467,657 | 8/1984 | Olsson | 73/861 |
| 5,209,258 | 5/1993 | Sharp et al. | 73/861.47 |
| 5,295,790 | 3/1994 | Bossart et al. | 73/861.52 |
| 5,408,886 | 4/1995 | Lalin | 73/861 |

Primary Examiner—Richard Chilcot
Assistant Examiner—Max Noori
Attorney, Agent, or Firm—E. Lieberstein

[57] ABSTRACT

A piston flow meter for measuring the flow of a gaseous fluid, such as ambient air, through the flow meter by timing the displacement of a piston in a hollow precision bore flowtube over a fixed distance. The piston is reciprocated from opposite ends of the flowtube by a poppet valve which controls the direction of movement of the piston in the flowtube. Ambient air is drawn into the flow tube from the atmosphere by an external pump connected to an inlet at one end of the flowtube. The flow meter includes a damping assembly for damping pulsations in gas flow through said flowtube with the damping assembly preferably located adjacent the pump inlet to the external pump. The damping assembly comprises damping means which includes a porous member and at least one elastic diaphragm contiguous thereto with the porous member having a multiplicity of voids and a plurality of open channels extending through the porous member to the elastic diaphragm.

13 Claims, 3 Drawing Sheets

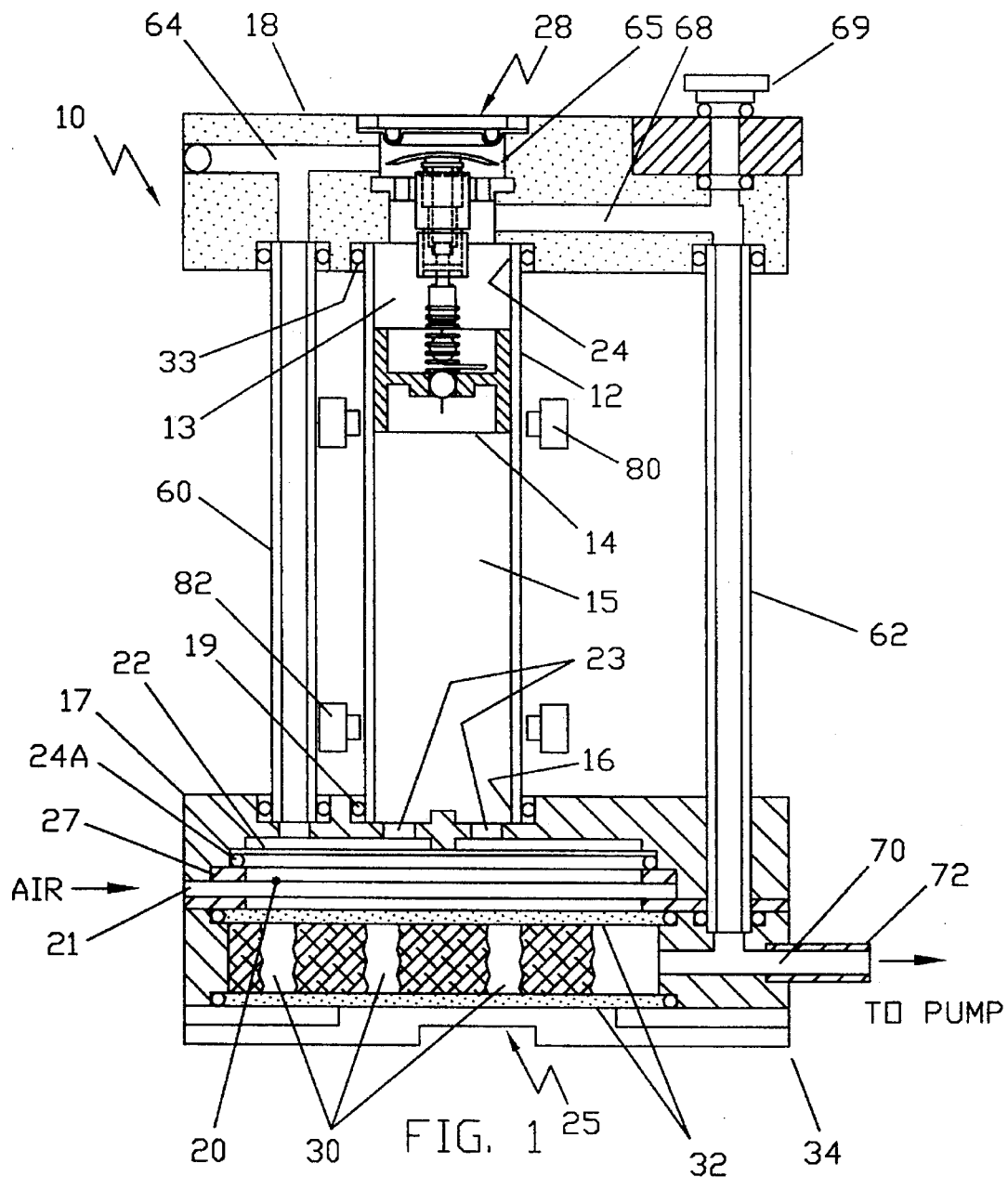
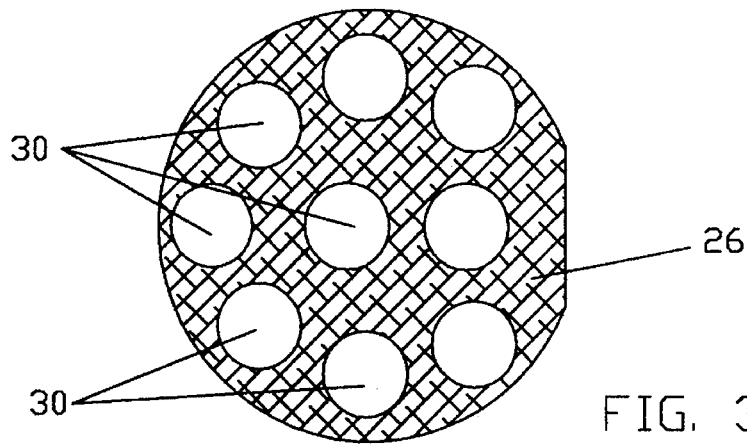
FIG. 1
FIG. 3

5,562,002

POSITIVE DISPLACEMENT PISTON FLOW METER WITH DAMPING ASSEMBLY

FIELD OF THE INVENTION

This invention relates to air flow measuring devices using a positive displacement piston flow meter and, more particularly, to a reciprocating piston flow meter having a damping assembly for smoothing out air flow pulses through the flow meter.

BACKGROUND OF INVENTION

The accurate measurement of ambient fluid (air) flow is becoming increasingly more important in the application and control of many processes, as well as in the research laboratory. One of the major applications is in the field of air sampling, in which an accurate knowledge of the sampled air quality determines the exposure level to various contaminants. The most widely accepted, primary standard method of flow measurement for a gaseous fluid is the bubble flow meter. In the basic form of the bubble flow meter, a soap film is generated from a soap solution, and is propelled by the gas flow under measurement from one end of the flow meter to the other. By timing the rise of the soap film between calibrated volume marks, the volume flow is obtained. Since for all practical purposes, the soap film is massless, it requires almost no force to accelerate the bubble. Furthermore, a seal is always insured by the presence of the bubble. Accordingly, a soap film flow meter comes closest to meeting the unique requirements of the ideal calibrator. However from the standpoint of convenience the use of a positive displacement flow meter in which a piston is reciprocated within a flowtube may have some practical advantages over the bubble flowmeter.

Nevertheless, the measurement of air flow using a positive displacement reciprocating piston flow meter is susceptible to errors due to the following:

a) Initial piston breakaway friction;
b) Acceleration and deceleration of the piston after breakaway (until equilibrium is reached);
c) Running friction within the flowtube; and
d) Fixed pressure loading determined by the mass of the piston.

Each of the above conditions present a load to the air flow system being measured. Moreover the suction pump which is used to draw air through the flowtube may cause air pulsations which in a positive displacement flow meter presents a dynamic load to the system. Various techniques for damping the air pulsations have been suggested heretofore with little success.

SUMMARY OF THE INVENTION

In accordance with the present invention it has been discovered that air pulsations through the flowtube may be minimized by incorporating a damping assembly in the flowmeter in communication with the air passageway to the external pump and responsive to pressure fluctuations in the flowtube. The preferred damping assembly of the present invention comprises a damping member composed of a porous element having a multiplicity of voids and a plurality of substantially parallel channels extending through the porous element with diaphragm means adjacent thereto.

The positive displacement piston flow meter of the present invention broadly comprises:

(a) a hollow flowtube having two opposite open ends;
(b) a piston disposed in said flowtube for movement between a first position relative to one of said open ends and a second position relative to the opposite open end thereof;
(c) means for connecting said flowtube to an external pump for directing a gaseous fluid through said flow meter at a flow rate to be measured by said flow meter;
(d) valve means for controllably reversing the direction of movement of said piston in said flowtube between said first and second position respectively; and
(e) damping means for damping pulsations in gas flow through said flowtube, said damping means comprising at least one elastic diaphragm responsive to pressure pulsations in said flowtube and a porous member contiguous thereto with the porous member having a multiplicity of voids distributed throughout the porous member and a plurality of open channels.

BRIEF DESCRIPTION OF THE DRAWINGS

Other features and advantages of the present invention will become apparent from the following detailed description of the invention when read in conjunction with the accompanying drawings of which:

FIG. 1 is a view in vertical section of a preferred embodiment of the piston flow meter of the present invention with the piston shown at the top of the piston stroke;

FIG. 3 is a bottom view of the damping element in the damping assembly of FIG. 1.

DETAILED DESCRIPTION OF THE INVENTION

Figure 2:
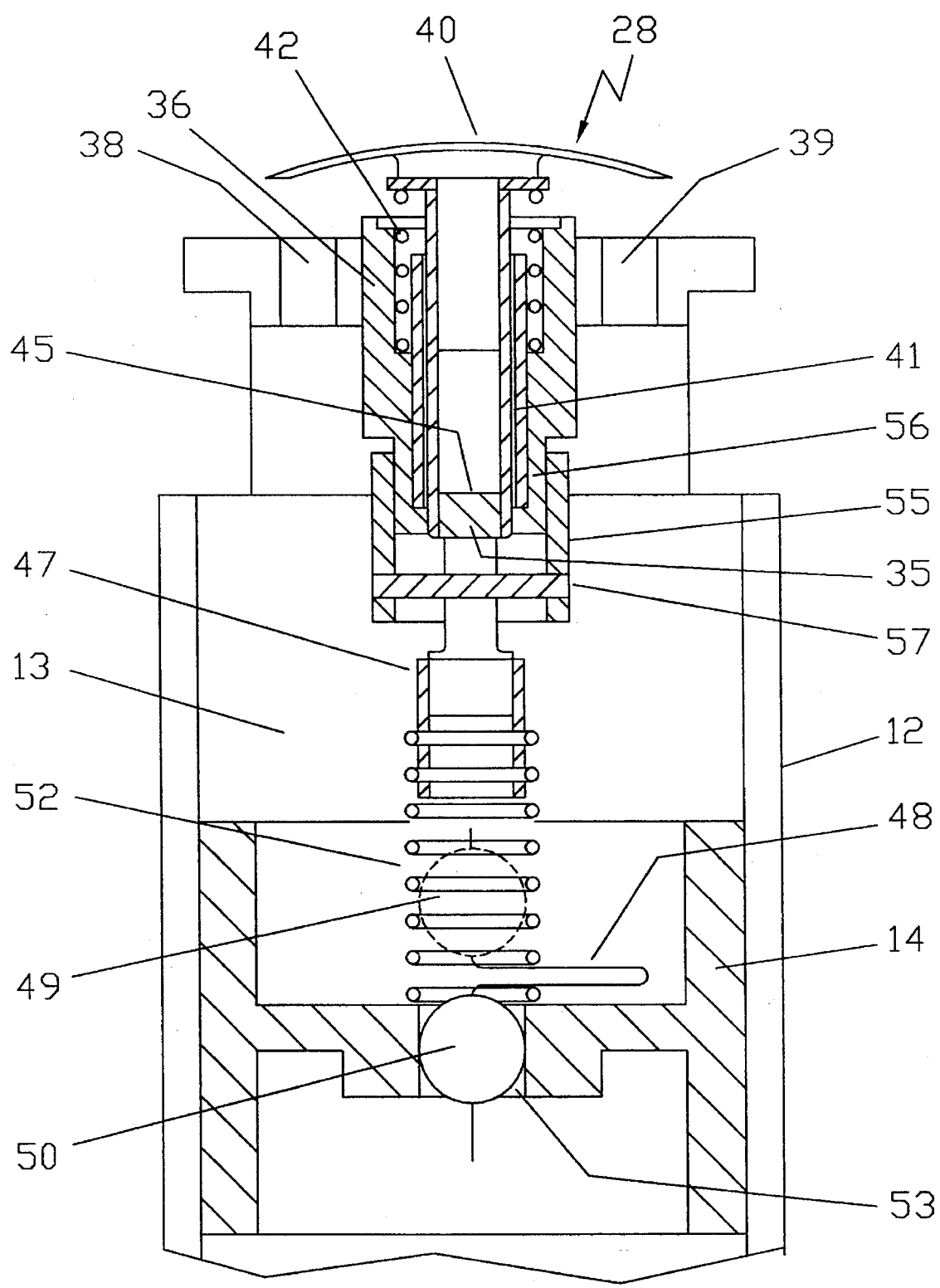
FIG. 2 is an exploded fragmentary view of a section of FIG. 1 illustrating the assembly of the preferred poppet valve for controlling the movement of the piston in the flowmeter of the present invention.
Figure 4:
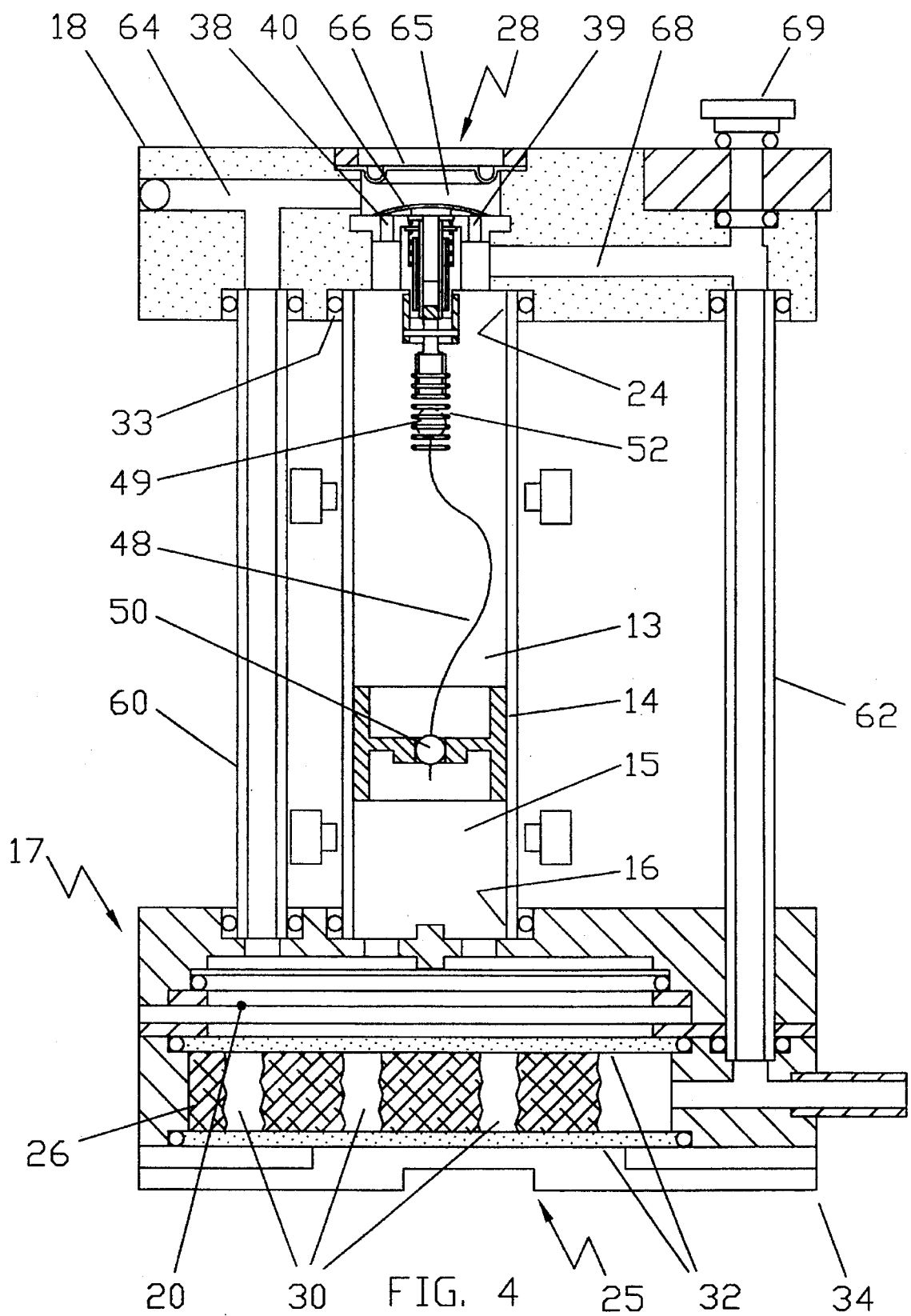
FIG. 4 is another view in vertical section of the piston flow meter of FIG. 1 with the piston shown rising from the bottom of the piston stroke.

The flow meter of the present invention is identified in FIG. 1 by the reference numeral (10), with its corresponding parts identified in each of the other figures by the same reference numbers. The flow meter (10) as shown in FIGS. 1, 2 and 4 comprises a hollow, cylindrical, open-ended precision bore flowtube (12) having a lightweight, smooth surface piston (14) fitted therein to a tight tolerance to provide substantially leakproof and frictionless movement. The piston (14) is composed of a solid material, such as graphite and reciprocates from a position adjacent the bottom end (16) of the flowtube (12) to an elevated position adjacent to the top end (24) of the flowtube (12) and back. The piston (14) separates the flowtube (12) into an upper piston chamber (13) located between the piston (14) and the top end (24) of the flowtube (12) and a lower piston chamber (15) located between the piston (14) and the bottom end (16) of the flowtube (12).

The flowtube (12) is preferably supported in a substantially vertical position between a lower housing (17) and an upper housing (18) although it should be understood that the flowtube (12) may equally be supported for operation in a horizontal position. In the vertical orientation the bottom end (16) of the flowtube (12) is mounted in the lower housing (17) and sealed from the atmosphere by an O-ring (19). The housing (17) has an internal chamber (20) which provides access to the atmosphere through an access passageway (21). The internal chamber (20) is accessable to the lower piston chamber (15) in the flowtube (12) through an air filter (22) and through openings (23) in the housing (17). The air filter (22) is supported by an o-ring (24a) held in place by a support ring (27) affixed to the housing (17). The housing (17) also includes a damping assembly (25) comprising a damper element (26) of a foam like-material containing a multiplicity of voids (not shown) and a plurality of open channels 30 extending between elastic diaphragm members (32) on opposite sides of the element (26). A bottom plate 34 holds the damping assembly 25 in place in the housing 17. The composition of the damper element (26) and its function will be discussed in greater detail later in the specification in connection with FIG. 3.

The top end (24) of the flowtube (12) is seated in housing (18) and sealed from leakage to the atmosphere by an o-ring (33). Housing (18) contains a poppet valve (28) for controlling the ascent and descent of the piston (14) in the flowtube (12). A preferred poppet valve arrangement is taught in U.S. Pat. No. 5,295,396 the disclosure of which is herein incorporated by reference. In general the poppet valve (28), as more specifically shown in FIG. 2, includes a valve body (36) including one or more valve openings (38) and (39) or a singular annular opening, an elastomeric valve head (40), a movable valve stem (41) which extends from the valve head (40) through the valve body (36), and a compression spring (42) seated in the valve body (36) around the valve stem (41).

The movable valve stem (41)is an elongated tubular member with an oval slot (not shown) in which a permanent magnet (45) is mounted. A mounting bracket (47), of cylindrical geometry extends from the valve stem (41) into the upper piston chamber (13). A flexible string (48) flexibly connects the mounting bracket (47) to the movable piston (14). The flexible string (48)is connected at one end to a spherical member (49) placed within a compression spring (52) mounted over the free end of the bracket (47). The compression spring (52) acts as a stop for the piston (14) during its ascent. The other end of the string (48) is connected to a spherical member (50) which is press fitted into an opening (53)in the piston (14). The flexible string (48) functions to automatically close the poppet valve (28) by pulling the movable valve stem (41) during the descent of the piston (14) when the piston (14) reaches a position at or near the bottom end (16) of the flowtube (12).

A cylindrical collar (55) extends over a depending section (56) of the valve body (36) surrounding the permanent magnet (35). The collar (55) has a steel pin (57) which extends through the oval slot (not shown) of the valve stem (41) to form a magnetic latch for holding the valve stem (41) in the valve closed position as shown in FIG. 4 with the flexible valve head (40) covering the valve opening(s) (38,39) in the valve body (36) against the force of the compression spring (42) until the piston (14) rises back to a position to open the valve (28) and to unlatch the magnet (35) from the steel pin (57) as shown in FIGS. 1 and 2. The collar (55) is adjustable to vary the magnetic latching force.

Two hollow tubes stand pipes (60) and (62) are respectively connected between the upper housing (18) and the lower housing (17). The hollow tube (60) communicates with a passageway (64) in the upper housing (18) and with the internal chamber (20) of the lower housing (17) through the air filter (22). The passageway (64) is in direct communication with an opening (65) above the valve head (40). A flexible diaphragm (66) is supported in the upper housing (18) in communication with the opening (65) above the valve head (40). When the valve (28) is open, as shown in FIGS. 1 and 2, the opening (65) is accessable to a passageway (68) in housing (18) through the valve openings (38) and (39). The passageway (68) leads into the upper piston chamber (13) of the flowtube (12) and is in communication with hollow tube (62) assuming the manually operable vent valve (69) is closed which is normally the case. The manually operable vent valve (69) permits single shot manual operation. The tube (62) communicates with an access passageway (70) to a pump inlet fitting (72) to which an external pump (not shown) is connected. The external pump (not shown), preferably a suction pump, draws gas (ambient air) from the inlet fitting (72) of the flowtube (10). The damping assembly (25) is positioned close to the access passageway (70) with one of the open channels (30) in direct communication with the inlet to the external pump.

As more clearly shown in FIG. 3 the damper element (26) in the damping assembly (25) is an open cell porous foam member preferably containing about 80 PPI (pores per inch). A multiplicity of open channels (30) is formed in the foam element (26). The number of open channels (30) and their size (diameter) may vary although a diameter of about ⅜ inch has been found to be satisfactory. The open channels (30) should be uniformly distributed and should preferably lie parallel to one another in a preferred direction substantially along the longitudinal axis of the flowmeter (10) between the two nonporous elastic diaphragms (32) (32) although the orientation of the channels 30 is not at all critical to the invention. The damping assembly (25) acts as an accumulator to smooth out pulsations in air flow through the flowmeter (10). The upper nonporous elastic diaphragm (32) separates the chamber (20) in the lower housing (17) from the access passageway (70) to the external pump. The damping assembly (25) is sensitive to pressure variations in the flowtube (10) with the parallel channels (30) substantially increasing the sensitivity of the damping element 26 to changes in air flow to and from the external pump so as to minimize flow variations.

In operation, referring to FIG. 4, with the valve (28) shown in the closed position and the pump inlet fitting (72) assumed to be attached to the suction side of a conventional vacuum pump and the manual vent valve (69) assumed to be in the manually closed position, air is drawn from the atmosphere through the air filter (22) and openings (23) into the lower piston chamber (15) of the flowtube (12) forcing the piston (14) to rise from a position at the bottom end of the flow meter (10) toward the upper end thereof. Upon reaching the upper end of the flow meter (12) the piston (14) will force the valve (28) into the open position as shown in FIGS. 1 and 2 by pushing the valve stem (41) upward to lift the valve head (40) off the valve openings (38) and (39) overcoming the magnetic latching force. Once the valve (28) is open air is drawn through the tube (60) to the passageway (68) and to the tube (62) thereby bypassing the valve (28) and the piston (14) begins to drop by gravity toward the bottom end of the flow tube (10). During the descent of the piston (14), the valve head (40)is maintained in the valve-open position by the compression spring (42). At the end of the piston stroke the flexible string (48) automatically closes the valve (28) by pulling the movable valve stem (41) down against the force of the compression spring (42) at a time when the piston (14) reaches a position at or near the bottom end (16) of the flowtube (12) and relatches the magnetic magnet (35) to the steel pin (57) so that the cycle may repeat itself, causing the piston (14) to ascend. Single stroke operation may be achieved by opening and closing the manual vent valve (69).

The flow meter (10) of the present invention will accurately measure the flow rate of a fluid pumped through the flow tube (12) over a wide range of flow rates. To measure flow through the flow tube (12) two sets of conventional optical LED photoelectric sensor elements (80) and (82) are positioned along the flowtube (12) spaced a fixed distance apart and operate to measure the displaced transit time of the leading and/or trailing edge of the piston (14) as it moves along the flowtube (12) between the two sets of sensor locations. The operation and and method of calculating transit time and flow rate is conventional and will not be discussed in this application.

What is claimed is:

1. A positive displacement piston flow meter comprising:

(a) a hollow flowtube having two opposite open ends;

(b) a piston disposed in said flowtube for movement between a first position relative to one of said open ends and a second position relative to the opposite open end thereof;

(c) means for connecting said flowtube to an external pump for directing a gaseous fluid through said flow meter at a flow rate to be measured by said flow meter;

(d) valve means for controllably reversing the direction of movement of said piston in said flowtube between said first and second position respectively; and (e) damping means for damping pulsations in gas flow through said flowtube, said damping means comprising at least one nonporous elastic diaphragm responsive to pressure pulsations in said flowtube and a porous member adjacent thereto with the porous member having a multiplicity of voids and a plurality of open channels extending to the elastic diaphragm and distributed throughout the porous member.

2. A piston flow meter as defined in claim 1 wherein said hollow flowtube is vertically oriented.

3. A piston flow meter as defined in claim 2 further comprising photoelectric sensor means arranged at different positions along said flowtube for detecting the presence of said piston at each such position.

4. A piston flow meter, as defined in claim 2, wherein said gaseous fluid is atmospheric air.

5. A piston flow meter, as defined in claim 4, wherein said plurality of open channels are arranged in a substantially parallel relationship to one another.

6. A piston flow meter, as defined in claim 5, further comprising another elastic diaphragm with said plurality of open channels extending therebetween.

7. A piston flow meter, as defined in claim 4, wherein valve means comprises a valve having a valve open position and a valve closed position, magnetic latch means for holding said valve in one of said positions and a flexible string connected to said piston and to said valve stem for automatically operating said magnetic latch means as the piston is moved from one end of the flow tube to the other.

8. A piston flow meter, as defined in claim 7, wherein said magnet is connected to said valve stem, and wherein said steel member is connected to said valve body such that when said valve assembly is in the valve-closed position, said steel member is magnetically latched to said magnet.

9. A piston flow meter, as defined in claim 8, wherein said valve assembly further comprises a manually adjustable member extending from said valve body, to which said steel member is affixed for adjusting the relative magnetic latching force between said magnet and said steel member.

10. A piston flow meter, as defined in claim 7, wherein said flexible string has one end affixed to a member mounted in a compression spring extending from said valve stem.

11. A piston flow meter, as defined in claim 10, wherein said flexible string has its opposite end affixed to a member attached to said piston.

12. A piston flow meter as defined in claim 1 wherein said means for connecting said flowtube to an external pump comprises an fitting with said damping means located in close proximity to said inlet fitting.

13. A piston flow meter as defined in claim 12 wherein at least one of said parallel channels is in direct unrestricted gaseous communication with said inlet fitting to the external pump.

* * * * *